(12) United States Patent
Filić et al.

(10) Patent No.: US 7,241,782 B1
(45) Date of Patent: Jul. 10, 2007

(54) POLYMORPH V OF TORASEMIDE

(75) Inventors: Darko Filić, Zagreb (HR); Miljenko Dumić, Zagreb (HR); Božena Klepić, Jastrebarsko (HR); Aleksandar Danilovski, Rijeka (HR); Marijan Tudja, Zagreb (HR)

(73) Assignee: PLIVA, farmaceutska industrija, dionicko drustvo (HR)

( * ) Notice: Subject to any disclaimer, the term of this patent is extended or adjusted under 35 U.S.C. 154(b) by 560 days.

(21) Appl. No.: 10/276,881

(22) PCT Filed: Sep. 25, 2000

(86) PCT No.: PCT/HR00/00033

§ 371 (c)(1),
(2), (4) Date: Jun. 11, 2003

(87) PCT Pub. No.: WO01/87841

PCT Pub. Date: Nov. 22, 2001

(30) Foreign Application Priority Data

May 19, 2000  (HR) .............................. P20000328 A

(51) Int. Cl.
*A61K 31/44* (2006.01)
*C07D 213/70* (2006.01)

(52) U.S. Cl. ...................... 514/345; 546/313
(58) Field of Classification Search ............... 546/313; 514/345
See application file for complete search history.

(56) References Cited

U.S. PATENT DOCUMENTS 4,018,929 A    4/1977  Delarge et al.
4,055,650 A    10/1977 Delarge et al.
RE30,633 E     6/1981  Delarge et al.
5,914,336 A *  6/1999  Dreckmann-Behrendt .. 514/347

FOREIGN PATENT DOCUMENTS

WO    WO 00/20395    4/2000

OTHER PUBLICATIONS

Masereel, B. et al, "Synthesis and pharmacology of pyrid-3-ylsufonylcyanoguanidines as diuretics," European Journal of Medicinal Chemistry, vol. 30, No. 4, 1995, p. 343-351.
Dupont, L. et al, "Structure d'une Seconde Variete de la Torasemide," Acta C. rystallography, Section B, Structural Crystallography and Crystal Chemistry, vol. B34, No. 8, Aug. 1978, pp. 2659-2662.
Dupont, L. et al, "Structure Cristalline et Moleculaire d'un Diuretique Derive de l'Alkyl-1[(Phenylamino-4-pyridyl-3)sulfonyl]-3 Uree: la Torasemide (C15H20N4SO3)," Acta Crystallography, Section B, Structural Crystallography and Crystal Chemistry, vol. B34, No. 4, Apr. 1978, pp. 1304-1310.

* cited by examiner

*Primary Examiner*—Joseph K. McKane
*Assistant Examiner*—Janet L. Coppins
(74) *Attorney, Agent, or Firm*—Connolly, Bove, Lodge & Hutz LLP

(57) ABSTRACT

The invention relates to a novel polymorph V of torasemide, to a process for its preparation, to its use as a raw material for the preparation of crystalline modifications I and III of torasemide, to amorphous torasemide modifications and to pharmaceutically acceptable salts of torasemide, to pharmaceutical forms containing the said novel polymorph V of torasemide as the active ingredient as well as to its use.

9 Claims, 3 Drawing Sheets

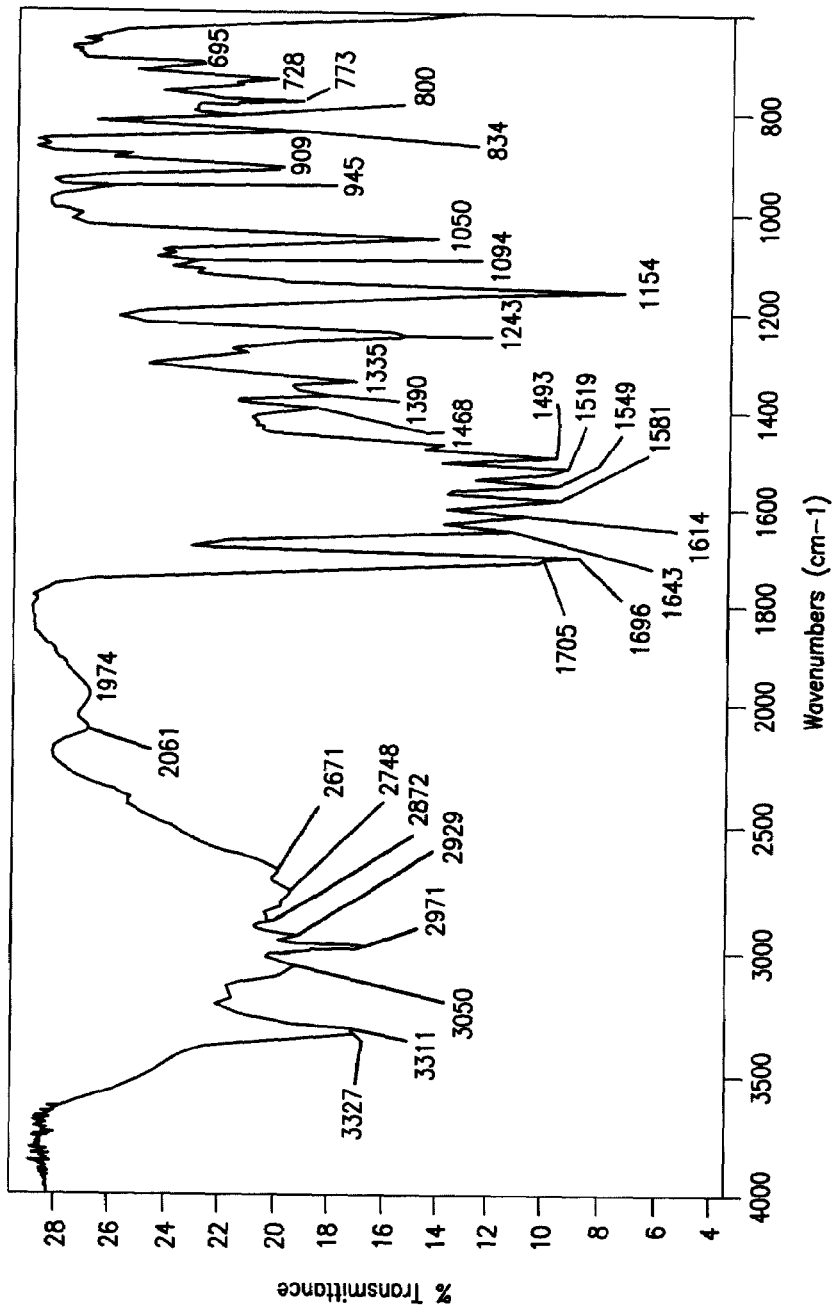

POLYMORPH V OF TORASEMIDE

The present invention relates to a novel crystalline form of N-(1-methylethyl aminocarbonyl)-4-(3-methyl-phenylamino)-3-pyridinesulfonamide (further referred to by its generic name "torasemide"), especially to a novel polymorph V of torasemide, to a process for its preparation, to its use as a raw material for the preparation of crystalline modifications I and III of torasemide, to amorphous torasemide modifications and to pharmaceutically acceptable salts of torasemide, to pharmaceutical forms containing the said novel polymorph V of torasemide as the active ingredient as well as to its use.

Torasemide is a new potent diuretic in the class of the so-called "loop diuretics", which is described in DE patent 25 16 025 (Example 71). Structurally, it entirely differs from diuretics of the same class such as furosemide, bumetanide and azosemide. In addition to diuretic properties it also possesses antihypertensive properties.

As a diuretic of Henle's loop it is useful as an agent for preventing heart or heart tissue damages caused by metabolic or ionic abnormalities associated with ischemia, in the treatment of thrombosis, angina pectoris, asthma, hypertension, nephroedema, pulmonary edema, primary and secondary aldosteronism, Bartter's syndrome, tumours, glaucoma, decreasing of intraocular pressure, acute or chronic bronchitis, in the treatment of cerebral edema caused by trauma, ischemia, concussion of the brain, metastases or epileptic attacks and in the treatment of nasal infections caused by allergens.

The ability of a substance to exist in more than one crystalline form is defined as polymorphism and these different crystalline forms are named "polymorph modifications" or "polymorphs". In general, polymorphism is caused by the ability of the molecule of a substance to change its conformation or to form different intermolecular and intramolecular interactions, particularly hydrogen bonds, which is reflected in different atom arrangements in the crystal lattices of different polymorphs. Polymorphism is found in several organic compounds. Among medicaments polymorphism is found in about 70% of barbiturates, 60% of sulfonamides and 60% of steroids, and about 50% of medicaments of the said classes are not present on the market in their most stable forms (T. Laird, Chemical Development and Scale-up in the Fine Chemical Industry, Principles and Practices, Course Manual, Scientific Update, Wyvern Cottage, 1996).

The different polymorphs of a substance possess different energies of the crystal lattice and, thus, they show different physical properties of the solid state such as form, density, melting point, colour, stability, dissolution rate, milling facility, granulation, compacting etc., which in medicaments may affect the possibility of the preparation of pharmaceutical forms, their stability, dissolution and bioavailability and, consequently, their action.

Polymorphism of medicaments is the object of studies of interdisciplinary expert teams [J. Haleblian, W. McCrone, *J. Pharm. Sci.* 58 (1969) 911; L. Borka, *Pharm. Acta Helv.* 66 (1991) 16; M. Kuhnert-Brandstätter, *Pharmazie* 51 (1996) 443; H. G. Brittain, *J. Pharm. Sci.* 86 (1997) 405; W. H. Streng, DDT 2 (1997) 415; K. Yoshii, *Chem. Pharm. Bull.* 45 (1997) 338, etc.]. A good knowledge of polymorphism represents a precondition for a critical observation of the whole process of medicament development. Thus, at deciding on the production of a pharmaceutical form in solid state and with regard to the dose size, stability, dissolution and anticipated action, it is necessary to determine the existence of all solid state forms (on the market some computer programmes can be found, e.g. >>Polymorph<< as a module of >>Cerius2<< programme, MSI Inc., USA) and to determine the physical-chemical properties of each of them. Only on the basis of these determinations the appropriate polymorph can be selected for the development of pharmaceutical formulations of desired properties.

From the great number of such efforts only a few will be mentioned as an example. Thus, Gordon et al. (U.S. Pat. No. 4,476,248) protected a novel crystallline form of ibuprofen and a process for the preparation thereof. Bunnel et al. (EP 733,635) protected a novel crystalline form, a process for the preparation thereof and pharmaceutical formulations of the drug olanzapine containing the said novel form. R. B. Gandhi et al. (EP 749,969) protected a novel process for the preparation of a polymorphous form I of stavudine from a mixture of one or more forms I, II and III, whereas A. Caron et al. (EP 708,103) protected a novel crystalline form of irbesartane, a process for the preparation thereof as well as pharmaceutical formulations containing this crystallline form. Chikaraishi et al. (WO 9626197) protected, in addition to a polymorphous form, also an amorphous form of piretanide as well as processes for the preparation thereof. J.-B. Cha et al. (WO 9857967) protected an amorphous form, a process for the preparation thereof and pharmaceutical formulations of the medicament itraconazole containing this amorphous form, whereas E. Occeli et al. (WO 90/00553) protected crystal polymorphs I and II and amorphs of the medicament rifapentine hydrochloride and hydrobromide. Further, for the new antidiabetic troglitazone G. Om Reddy et al. (U.S. Pat. No. 5,700,820) protected six polymorphs: five crystal polymorphs and one amorphous one.

It is known that torasemide can exist in three crystalline modifications differing with regard to the parameters of a unit cell, which is confirmed by X-ray diffraction on their monocrystals, and in one amorphous modification (HR patent application P20000162A). Modification I with melting point 169° C. [*Acta Cryst.* B34 (1978), 1304–1310] and modification III with melting point 165° C. (WO 00/20395) crystallize monoclinically in the space group P $2_1$/c (prisms), while modification II with melting point 162° C. crystallizes monoclinically in the space group P 2/n (foils) [*Acta Cryst.* B34 (1978), 2659–2662].

In addition to the above, U.S. Pat. No. 5,914,336 protected the use of a new torasemide polymorph, however, only some of its physical-chemical properties such as melting point, heat of formation, solubility, first band in IR-spectrum, but no X-ray patterns of the powder and monocrystals were stated therein. Since the data as stated are not relevant for the characterization of polymorphism, the claimed subject-matter of U.S. Pat. No. 5,914,336 is not believed to be reliable.

In our further research in the field of torasemide we have surprisingly found a novel crystalline torasemide modification, i.e. a novel polymorph V of torasemide which has hitherto not been known.

The novel polymorph V of torasemide is prepared according to the inventive process in the form of a flowable crystalline powder having the property of flowability, i.e. it is obtained in a "free-flow" form which is statically not chargeable.

In a solution the novel polymorph V of torasemide is identical to other known torasemide modifications, which is evident from NMR and UV spectra. On the other hand, solid state analysis techniques such as differential scanning calorimetry (DSC), X-ray powder pattern (XRD) and IR spectroscopy reveal a difference in comparison to the known torasemide modifications.

DSC of the novel polymorph V of torasemide (FIG. 1) shows one exothermic maximum at about 157.59° C. (onset at about 150.74° C.) (heating rate of 10° C./min) resulting from decomposition (also evident on the basis of IR spectroscopy and thin-layer chromatography).

The X-ray powder pattern of the novel polymorph V of torasemide differs from the X-ray powder patterns of the known torasemide modifications (FIG. 2).

The IR spectrum of a sample of the novel polymorph V of torasemide recorded in KBr (FIG. 3) differs from IR spectra of the known torasemide modifications. The novel polymorph V of torasemide shows characteristic absorption bands at 2671 to 3327 cm$^{-1}$ and at 1468 to 1705 cm$^{-1}$.

FIG. 3 represents a characteristic IR spectrum of the novel polymorph V of torasemide recorded in KBr.

The novel polymorph V of torasemide according to the present invention can be obtained by a rapid acidification of alkaline torasemide solutions with inorganic or organic acids.

Figure 1:
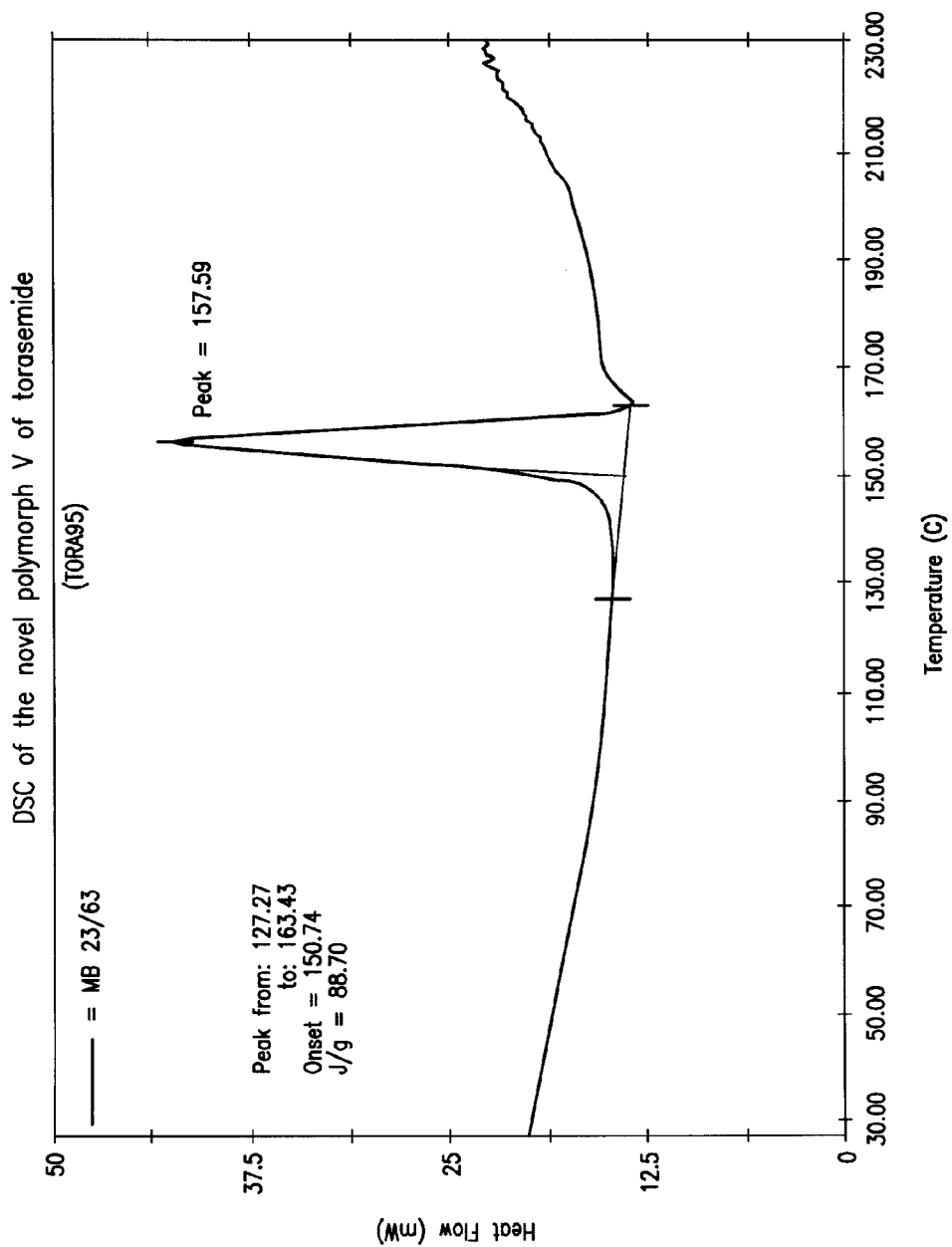
FIG. 1 represents a characteristic thermogram of differential scanning calorimetry (DSC) of the novel polymorph V of torasemide.
Figure 2:
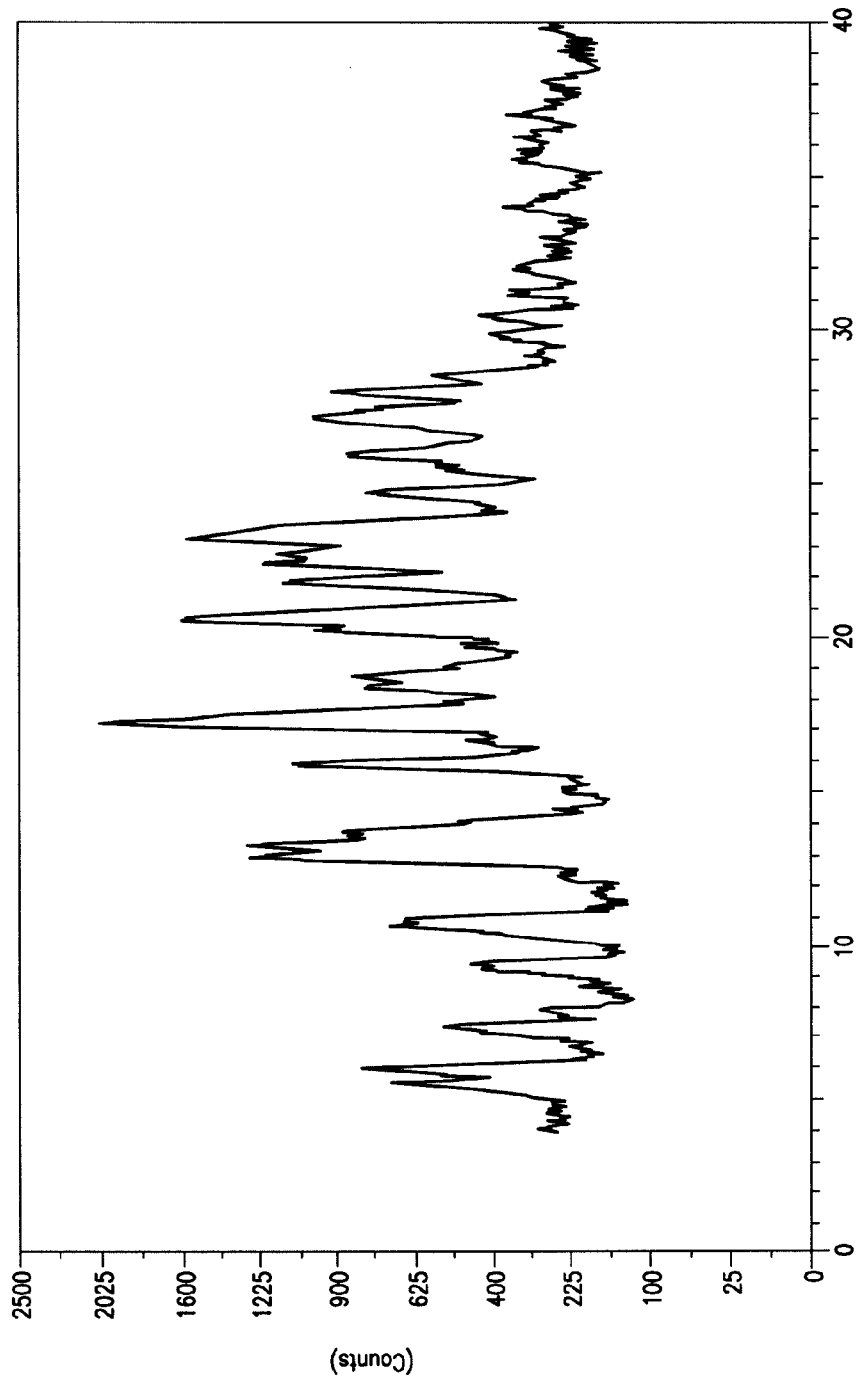
FIG. 2 represents a characteristic X-ray powder pattern of the novel polymorph V of torasemide.

A process for the preparation of the novel polymorph V of torasemide comprises:

(i) the preparation of a polymorph I of torasemide according to a known process, (ii) the dissolution of the polymorph I of torasemide in an aqueous solution of a base, (iii) the filtration of the obtained solution, (iv) a rapid acidification of the obtained solution with an aqueous solution of an acid at temperatures between 0° C. and 35° C., (v) the filtration of the obtained suspension, (vi) washing the thus obtained crystals of the novel polymorph V of torasemide with demineralized water and drying them in a vacuum dryer during 3 hours at 50° C., the obtained crystals being characterized by the following data:

DSC: exothermic maximum at about 157.59° C. (onset at about 150.74° C.) (FIG. 1);

X-ray powder pattern (2 Θ): 5.610; 6.130; 7.480; 7.970; 9.310; 9.615; 10.835; 11.020; 12.340; 13.075; 13.460; 13.920; 14.200; 15.090; 16.080; 16.710; 17.445; 17.720; 18.460; 18.850; 19.825; 20.340; 20.990; 21.980; 22.075; 22.630; 22.935; 23.410; 23.845; 24.880; 25.560; 26.035; 27.285; 27.540; 28.170; 28.645; 29.350; 29.975; 30.575; 31.265; 32.300; 34.050; 35.650; 36.375; 37.100, and 38.145 (FIG. 2);

IR-characteristic absorption bands (cm$^{-1}$): at 2671 to 3327 and at 1468 to 1705 (FIG. 3).

According to a further embodiment of the present invention, a process for the preparation of the novel polymorph V of torasemide also comprises:

(i) the preparation of a polymorph II of torasemide according to a known process, (ii) the dissolution of the polymorph II of torasemide in an aqueous solution of a base, (iii) the filtration of the obtained solution, (iv) a rapid acidification of the obtained solution with an aqueous solution of an acid at temperatures between 0° C. and 35° C., (v) the filtration of the obtained suspension, (vi) washing the thus obtained crystals of the novel polymorph V of torasemide with demineralized water and drying them in a vacuum dryer during 3 hours at 50° C., the obtained crystals being characterized by the data represented in the previous process.

According to a further embodiment of the present invention, a process for the preparation of the novel polymorph V of torasemide also comprises:

(i) the preparation of a polymorph III of torasemide according to a known process, (ii) the dissolution of the polymorph III of torasemide in an aqueous solution of a base, (iii) the filtration of the obtained solution, (iv) a rapid acidification of the obtained solution with an aqueous solution of an acid at temperatures between 0° C. and 35° C., (v) the filtration of the obtained suspension, (vi) washing the thus obtained crystals of the novel polymorph V of torasemide with demineralized water and drying them in a vacuum dryer during 3 hours at 50° C., the obtained crystals being characterized by the data represented in the previous process.

According to a further embodiment of the present invention, a process for the preparation of the novel polymorph V of torasemide also comprises:

(i) the preparation of an amorphous torasemide modification according to a known process, (ii) the dissolution of the amorphous torasemide modification in an aqueous solution of a base, (iii) the filtration of the obtained solution, (iv) a rapid acidification of the obtained solution with an aqueous solution of an acid at temperatures between 0° C. and 35° C., (v) the filtration of the obtained suspension, (vi) washing the thus obtained crystals of the novel polymorph V of torasemide with demineralized water and drying them in a vacuum dryer during 3 hours at 50° C., the obtained crystals being characterized by the data represented in the previous process.

According to a further embodiment of the present invention, a process for the preparation of the novel polymorph V of torasemide also comprises:

(i) the preparation of a novel polymorph V of torasemide according to the process of the present invention, (ii) the dissolution of the novel polymorph V of torasemide in an aqueous solution of a base, (iii) the filtration of the obtained solution, (iv) a rapid acidification of the obtained solution with an aqueous solution of an acid at temperatures between 0° C. and 35° C., (v) the filtration of the obtained suspension, (vi) washing the thus obtained crystals of the novel polymorph V of torasemide with demineralized water and drying them in a vacuum dryer during 3 hours at 50° C., the obtained crystals being characterized by the data represented in the previous process.

According to a further embodiment of the present invention, a process for the preparation of the novel polymorph V of torasemide also comprises:

(i) the preparation of polymorphs I, II and II of torasemide according to known processes, the preparation of an amorphous torasemide modification according to a known process and the preparation of the novel polymorph V of torasemide according to the process of the present invention, (ii) the dissolution of any mixture of the polymorphs I, II and III of torasemide, of the amorphous torasemide modification or the novel polymorph V of torasemide in an aqueous solution of a base, (iii) the filtration of the obtained solution, (iv) a rapid acidification of the obtained solution with an aqueous solution of an acid at temperatures between 0° C. and 35° C., (v) the filtration of the obtained suspension, (vi) washing the thus obtained crystals of the novel polymorph V of torasemide with demineralized water and drying them in a vacuum dryer during 3 hours at 50° C., the obtained crystals being characterized by the data represented in the previous process.

According to the present process, aqueous solutions of lithium hydroxide, sodium hydroxide and potassium hydroxide as well as aqueous solutions of sodium carbonate and potassium carbonate may be used for the preparation of alkaline solutions of torasemide modifications.

The acidification of alkaline torasemide solutions may, according to the present process, be carried out with inorganic acids such as hydrochloric, sulfuric, phosphoric and nitric acids, and with organic acids such as formic, acetic, propionic, oxalic, tartaric, methanesulfonic and p-toluenesulfonic acids.

It has also been established that at using the present process no decomposition of torasemide takes place, i.e. a chemically pure novel polymorph V of torasemide (TLC and HPLC) is obtained.

It has been additionally established that under normal storage conditions the novel polymorph V of torasemide is stable at milling and pressing, i.e. it is not transformed into crystalline modifications I, II and III of torasemide or into an amorphous torasemide modification.

The novel polymorph V of torasemide prepared according to the present process may be converted to crystalline modifications I, II or III of torasemide or to an amorphous torasemide modification according to conventional processes, i.e. it may serve as a starting material for the preparation of well-known crystalline modifications I, II or III of torasemide or an amorphous torasemide modification.

The novel polymorph V of torasemide prepared according to the present invention may be converted into pharmaceutically acceptable salts of torasemide in a well-known manner.

The examination of the release (USP 24) of the novel polymorph V of torasemide in water in comparison with the release profile of known crystalline torasemide modifications in the same medium revealed a slower release thereof. This makes the novel polymorph V of torasemide suitable for the preparation of pharmaceutical preparations having immediate or prolonged action.

The novel polymorph V of torasemide prepared according to the present process may be, as a suitable torasemide form, used as a diuretic or as an agent for preventing heart or heart tissue damages caused by metabolic or ionic abnormalities associated with ischemia, in the treatment of thrombosis, angina pectoris, asthma, hypertension, nephroedema, pulmonary edema, primary and secondary aldosteronism, Bartter's syndrome, tumours, glaucoma, decreasing of intraocular pressure, acute or chronic bronchitis, in the treatment of cerebral edema caused by trauma, ischemia, concussion of the brain, metastases or epileptic attacks and in the treatment of nasal infections caused by allergens.

The present invention also relates to pharmaceutical forms such as tablets, capsules or injections containing an effective amount of the novel polymorph V of torasemide as an active ingredient, without or in combination with one or more pharmaceutically acceptable additives such as sugar, starch, starch derivatives, cellulose, cellulose derivatives, mould release agents, and antiadhesive agents and, possibly, agents for regulating flowability.

The present invention is illustrated by the following non-limiting Examples.

EXAMPLE 1

The crystalline modification I of torasemide (1.0 g) prepared according to *Acta Cryst.* B34 (1978) 1304–1310, was dissolved in a 5% aqueous sodium hydroxide solution (3 ml) and then at the temperature of 20° C. the solution was acidified for 15 seconds with a 5% aqueous hydrochloric acid solution. The crystals were sucked off, washed with demineralized water and acetone and dried in a vacuum dryer for 3 hours at 50° C. A chemically pure novel polymorph V of torasemide (0.9 g), m.p. 153–155° C. was obtained.

The characteristic DSC curve of the sample as shown in FIG. 1 was recorded on the apparatus Perkin-Elmer DSC7 at a heating rate of 10° C./minute.

The characteristic X-ray powder pattern as shown in FIG. 2 was recorded on the instrument PHILIPS PW3710 under Cu X-rays [$\lambda(CuK\alpha_1)$=1.54046 Å and $\lambda(CuK\alpha_2)$ 1.54439 Å].

The characteristic IR spectrum of the sample as shown in FIG. 3 was recorded in KBr on the IR-spectrophotometer Nicolet-Magna 760.

EXAMPLE 2

The crystalline modification II of torasemide (1.0 g) prepared according to *Acta Cryst.* B34 (1978) 1304–1310, was dissolved in a 5% aqueous potassium hydroxide solution (3 ml) and then at the temperature of 20° C. the solution was acidified for 15 seconds with a 10% aqueous acetic acid solution. The crystals were sucked off, washed with demineralized water and acetone and dried in a vacuum dryer for 3 hours at 50° C. A chemically pure novel polymorph V of torasemide (0.9 g), m.p. 153–155° C. was obtained.

The IR spectrum of the sample thus obtained corresponded to the IR spectrum of the novel polymorph V of torasemide obtained according to Example 1.

EXAMPLE 3

The crystalline modification III of torasemide (10.0 g) prepared according to WO 00/20395, was dissolved in a 10% aqueous sodium carbonate solution (30 ml) and then at the temperature of 20° C. the solution was acidified for 60 seconds with a 5% aqueous sulfuric acid solution. The crystals were sucked off, washed with demineralized water and acetone and dried in a vacuum dryer for 3 hours at 50° C. A chemically pure novel polymorph V of torasemide (8.1 g), m.p. 153–155° C. was obtained.

The IR spectrum of the sample thus obtained corresponded to the IR spectrum of the novel polymorph V of torasemide obtained according to Example 1.

EXAMPLE 4

The amorphous torasemide modification (10.0 g) prepared according to HR patent application P20000162A, was dissolved in a 10% aqueous potassium carbonate solution (30 ml) and then at the temperature of 20° C. the solution was acidified for 90 seconds with a 10% aqueous tartaric acid solution. The crystals were sucked off, washed with demineralized water and acetone and dried in a vacuum dryer for 3 hours at 50° C. A chemically pure novel polymorph V of torasemide (8.0 g), m.p. 153–155° C. was obtained.

The IR spectrum of the sample thus obtained corresponded to the IR spectrum of the novel polymorph V of torasemide obtained according to Example 1.

EXAMPLE 5

The novel polymorph V of torasemide (10.0 g) according to Example 3 of the present invention was dissolved in a 5% aqueous lithium hydroxide solution (30 ml) and then at the temperature of 20° C. the solution was acidified for 120 seconds with a 5% aqueous phosphoric acid solution. The crystals were sucked off, washed with demineralized water and acetone and dried in a vacuum dryer for 3 hours at 50° C. A chemically pure novel polymorph V of torasemide (7.9 g), m.p. 153–155° C. was obtained.

The IR spectrum of the sample thus obtained corresponded to the IR spectrum of the novel polymorph V of torasemide obtained according to Example 1.

EXAMPLE 6

A mixture (1.0 g) of crystalline modifications I and II of torasemide prepared according to *Acta Cryst*. B34 (1978) 1304–1310, was dissolved in a 10% aqueous sodium carbonate solution (3 ml) and then at the temperature of 20° C. the solution was acidified for 15 seconds with a 5% aqueous p-toluenesulfonic acid solution. The crystals were sucked off, washed with demineralized water and acetone and dried in a vacuum dryer for 3 hours at 50° C. A chemically pure novel polymorph V of torasemide (0.9 g), m.p. 153–155° C. was obtained.

The IR spectrum of the sample thus obtained corresponded to the IR spectrum of the novel polymorph V of torasemide obtained according to Example 1.

EXAMPLE 7

A mixture (1.0 g) of crystalline modifications I and III of torasemide prepared according to *Acta Cryst*. B34 (1978) 1304–1310 and WO 00/20395, was dissolved in a 5% aqueous sodium hydroxide solution (3 ml) and then at the temperature of 20° C. the solution was acidified for 15 seconds with a 5% aqueous nitric acid solution. The crystals were sucked off, washed with demineralized water and acetone and dried in a vacuum dryer for 3 hours at 50° C. A chemically pure novel polymorph V of torasemide (0.9 g), m.p. 153–155° C. was obtained.

The IR spectrum of the sample thus obtained corresponded to the IR spectrum of the novel polymorph V of torasemide obtained according to Example 1.

EXAMPLE 8

A mixture (1.0 g) of crystalline modifications II and III of torasemide prepared according to *Acta Cryst*. B34 (1978) 1304–1310 and WO 00/20395, was dissolved in a 5% aqueous potassium hydroxide solution (3 ml) and then at the temperature of 20° C. the solution was acidified for 15 seconds with a 10% aqueous propionic acid solution. The crystals were sucked off, washed with demineralized water and acetone and dried in a vacuum dryer for 3 hours at 50° C. A chemically pure novel polymorph V of torasemide (0.9 g), m.p. 153–155° C. was obtained.

The IR spectrum of the sample thus obtained corresponded to the IR spectrum of the novel polymorph V of torasemide obtained according to Example 1.

EXAMPLE 9

A mixture (1.0 g) of crystalline modifications I, II and III of torasemide prepared according to *Acta Cryst*. B34 (1978) 1304–1310 and WO 00/20395, was dissolved in a 5% aqueous lithium hydroxide solution (3 ml) and then at the temperature of 20° C. the solution was acidified for 15 seconds with a 10% aqueous oxalic acid solution. The crystals were sucked off, washed with demineralized water and acetone and dried in a vacuum dryer for 3 hours at 50° C. A chemically pure novel polymorph V of torasemide (0.9 g), m.p. 153–155° C. was obtained.

The IR spectrum of the sample thus obtained corresponded to the IR spectrum of the novel polymorph V of torasemide obtained according to Example 1.

EXAMPLE 10

A mixture (1.0 g) of a crystalline modification I of torasemide and an amorphous torasemide modification prepared according to *Acta Cryst*. B34 (1978) 1304–1310 and HR patent application P20000162A, was dissolved in a 10% aqueous sodium carbonate solution (3 ml) and then at the temperature of 20° C. the solution was acidified for 15 seconds with a 5% aqueous methanesulfonic acid solution. The crystals were sucked off, washed with demineralized water and acetone and dried in a vacuum dryer for 3 hours at 50° C. A chemically pure novel polylmorph V of torasemide (0.9 g), m.p. 153–155° C. was obtained.

The IR spectrum of the sample thus obtained corresponded to the IR spectrum of the novel polymorph V of torasemide obtained according to Example 1.

EXAMPLE 11

A mixture (1.0 g) of a crystalline modification I of torasemide and of the novel polymorph V of torasemide prepared according to *Acta Cryst*. B34 (1978) 1304–1310 and according to Example 1 of the present invention, was dissolved in a 10% aqueous potassium carbonate solution (3 ml) and then at the temperature of 20° C. the solution was acidified for 15 seconds with a 5% aqueous hydrochloric acid solution. The crystals were sucked off, washed with demineralized water and acetone and dried in a vacuum dryer for 3 hours at 50° C. A chemically pure novel polymorph V of torasemide (0.9 g), m.p. 153–155° C. was obtained.

The IR spectrum of the sample thus obtained corresponded to the IR spectrum of the novel polymorph V of torasemide obtained according to Example 1.

EXAMPLE 12

A mixture (10.0 g) of crystalline modifications I, II and III of torasemide, of an amorphous torasemide modification and of the novel polymorph V of torasemide prepared according to *Acta Cryst.* B34 (1978) 1304–1310, WO 00/20395, HR patent application P20000162A and Example 1 of the present invention, was dissolved in a 5% aqueous sodium hydroxide solution (30 ml) and then at the temperature of 20° C. the solution was acidified for 60 seconds with a 10% aqueous acetic acid solution. The crystals were sucked off, washed with demineralized water and acetone and dried in a vacuum dryer for 3 hours at 50° C. A chemically pure novel polymorph V of torasemide (8.0 g), m.p. 153–155° C. was obtained.

The IR spectrum of the sample thus obtained corresponded to the IR spectrum of the novel polymorph V of torasemide obtained according to Example 1.

EXAMPLE 13

The novel polymorph V of torasemide obtained according to Example 1 of the present invention was subjected to testing the release of the active substance in water at the temperature of 37° C. (USP 24) and the results are given in Table 1.

TABLE 1

Release of the novel polymorph V of torasemide in water (USP 24) (37° C., 50 rpm, 1000 ml)

| Time (min) | Released torasemide (%) |
|---|---|
| 0 | 0 |
| 15 | 11.3 |
| 30 | 20.5 |
| 45 | 26.0 |
| 60 | 30.0 |
| 90 | 36.0 |
| 120 | 40.7 |

The invention claimed is:

1. Polymorph V of torasemide characterized by the following data:
   DSC: exothermic maximum at about 157.59° C. (onset at about 150.74° C.) with the heating rate of 10° C./min;
   X-ray powder pattern (2 Θ): 5.610; 6.130; 7.480; 7.970; 9.310; 9.615; 10.835; 11.020; 12.340; 13.075; 13.460; 13.920; 14.200; 15.090; 16.080; 16.710; 17.445; 17.720; 18.460; 18.850; 19.825; 20.340; 20.990; 21.980; 22.075; 22.630; 22.935; 23.410; 23.845; 24.880; 25.560; 26.035; 27.285; 27.540; 28.170; 28.645; 29.350; 29.975; 30.575; 31.265; 32.300; 34.050; 35.650; 36.375; 37.100, and 38.145;
   IR-characteristic absorption bands at 2671 to 3327 and at 1468 to 1705 cm$^{-1}$.

2. Polymorph V of torasemide according to claim 1, characterized in that it is chemically pure.

3. Polymorph V of torasemide according to claim 1, characterized in that it contains no water.

4. Polymorph V of torasemide according to claim 1, characterized in that it contains no solvent.

5. Process for the preparation of the polymorph V of torasemide according to claim 1, characterized in that an alkaline solution of torasemide is subjected to a rapid acidification with inorganic or organic acids at temperatures between 0° C. and 35° C.

6. Process for the preparation of the polymorph V of torasemide according to claim 5, wherein said torasemide is selected from the group consisting of crystalline modifications I, II and III of torasemide, an amorphous torasemide modification or the polymorph V of torasemide, and any mutual mixture of said crystalline modifications I, II and III of torasemide, and said an amorphous torasemide modification; and mixtures thereof with the polymorph V of torasemide.

7. Process for the preparation of the polymorph V of torasemide according to claim 5, wherein said alkaline solutions of torasemide is selected from the group consisting of aqueous solutions of lithium hydroxide, sodium hydroxide potassium hydroxide sodium carbonate and potassium carbonate.

8. Process for the preparation of the polymorph V of torasemide according to claim 5, wherein said acids are selected from the group consisting of hydrochloric, sulfuric, phosphoric, nitric, formic, acetic, propionic, oxalic, tartaric, methanesulfonic and p-toluenesulfonic.

9. A pharmaceutically acceptable salt of the polymorph V of torasemide characterized by the following data:
   DSC: exothermic maximum at about 157.59° C. (onset at about 150.74° C.) with the heating rate of 10° C./min;
   X-ray powder pattern (2 Θ): 5.610; 6.130; 7.480; 7.970; 9.310; 9.615; 10.835; 11.020; 12.340; 13.075; 13.460; 13.920; 14.200; 15.090; 16.080; 16.710; 17.445; 17.720; 18.460; 18.850; 19.825; 20.340; 20.990; 21.980; 22.075; 22.630; 22.935; 23.410; 23.845; 24.880; 25.560; 26.035; 27.285; 27.540; 28.170; 28.645; 29.350; 29.975; 30.575; 31.265; 32.300; 34.050; 35.650; 36.375; 37.100, and 38.145;
   IR-characteristic absorption bands at 2671 to 3327 and at 1468 to 1705 cm$^{-1}$.

* * * * *